US010722684B2

(12) United States Patent
Soltis et al.

(10) Patent No.: US 10,722,684 B2
(45) Date of Patent: Jul. 28, 2020

(54) LEADLESS DELIVERY CATHETER WITH CONDUCTIVE PATHWAY

(71) Applicant: CARDIAC PACEMAKERS, INC., St. Paul, MN (US)

(72) Inventors: Brian Soltis, St. Paul, MN (US); Brendan E. Koop, Ham Lake, MN (US); Benjamin J. Haasl, Forest Lake, MN (US); Kurt G. Koubal, Mound, MN (US); James P. Goodman, Shorewood, MN (US); Vincent P. Hackenmueller, Elk River, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 174 days.

(21) Appl. No.: 15/852,299

(22) Filed: Dec. 22, 2017

(65) Prior Publication Data

US 2018/0177979 A1   Jun. 28, 2018

Related U.S. Application Data

(60) Provisional application No. 62/439,259, filed on Dec. 27, 2016.

(51) Int. Cl.
*A61N 1/372* (2006.01)
*A61M 25/00* (2006.01)
(Continued)

(52) U.S. Cl.
CPC .... *A61M 25/0082* (2013.01); *A61M 25/0068* (2013.01); *A61M 25/0097* (2013.01);
(Continued)

(58) Field of Classification Search
CPC ........ A61N 1/05; A61N 1/056; A61N 1/0565; A61N 2001/0578; A61N 2001/058;
(Continued)

(56) References Cited

U.S. PATENT DOCUMENTS 4,301,815 A   11/1981   Doring
5,807,399 A   9/1998   Laske et al.
(Continued)

FOREIGN PATENT DOCUMENTS

EP   2818201 B1   7/2016
EP   2658599 B1   10/2016
(Continued)

OTHER PUBLICATIONS

International Search Report and Written Opinion dated Mar. 6, 2018 for International Application No. PCT/US2017068143.

*Primary Examiner* — Eugene T Wu
(74) *Attorney, Agent, or Firm* — Seager, Tufte & Wickhem LLP

(57) ABSTRACT

Catheter and implantable leadless pacing devices, systems, and methods utilizing catheters and implantable leadless pacing devices are disclosed. An example catheter system may include a holding structure extending distally from a tubular member. An implantable device, such as a leadless pacing device, may be located within a cavity of the holding structure. The holding structure may include one or more electrical ports adjacent the proximal end of the holding structure and adjacent or proximal of the proximal end of the implantable device. The electrical ports may provide a conductive pathway extending through the distal structure to allow electrical signals to pass through the distal structure to and/or from the implantable device.

9 Claims, 14 Drawing Sheets

(51) Int. Cl.
*A61N 1/375* (2006.01)
*A61N 1/05* (2006.01)
*A61N 1/368* (2006.01)
*A61M 25/01* (2006.01)

(52) U.S. Cl.
CPC ......... *A61N 1/0587* (2013.01); *A61N 1/3756* (2013.01); *A61N 1/37211* (2013.01); *A61N 1/37288* (2013.01); *A61N 1/37512* (2017.08); *A61N 1/37518* (2017.08); A61M 25/0014 (2013.01); A61M 2025/0004 (2013.01); A61M 2025/0175 (2013.01); A61N 1/0573 (2013.01); A61N 1/368 (2013.01); A61N 1/37205 (2013.01); A61N 1/37217 (2013.01); A61N 2001/058 (2013.01)

(58) Field of Classification Search
CPC ........ A61N 2001/362; A61N 2001/372; A61N 2001/37205; A61N 2001/37211; A61N 2001/37217; A61N 2001/37294; A61N 2001/375; A61N 2001/3756
See application file for complete search history.

(56) References Cited

U.S. PATENT DOCUMENTS

| | | |
|---|---|---|
| 5,908,381 A | 6/1999 | Aznoian et al. |
| 6,181,973 B1 | 1/2001 | Ceron et al. |
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bomzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bomzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2013/0012925 A1 | 1/2013 | Berthiaume et al. |
| 2013/0035636 A1 | 2/2013 | Beasley et al. |
| 2013/0103047 A1 | 4/2013 | Steingisser et al. |
| 2013/0253342 A1 | 9/2013 | Griswold et al. |
| 2013/0253346 A1 | 9/2013 | Griswold et al. |
| 2014/0018818 A1 | 1/2014 | Somogyi et al. |
| 2014/0324145 A1 | 10/2014 | Eggen et al. |

(56) References Cited

U.S. PATENT DOCUMENTS

| | | |
|---|---|---|
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1* | 2/2015 | Schmidt ............ A61M 25/0082 606/129 |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0015968 A1* | 1/2016 | Bonner ................ A61N 1/0592 606/129 |
| 2016/0015983 A1* | 1/2016 | Sheldon ................ A61N 1/371 606/129 |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114156 A1* | 4/2016 | Haasl .................. A61N 1/0587 606/129 |
| 2016/0114157 A1 | 4/2016 | Haasl et al. |
| 2016/0158560 A1 | 6/2016 | Moore et al. |
| 2016/0175599 A1 | 6/2016 | Hastings et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1* | 9/2016 | Ollivier ................ A61N 1/375 |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bomzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |
| 2018/0140855 A1* | 5/2018 | Kane .................. A61N 1/37512 |
| 2018/0177979 A1 | 6/2018 | Soltis |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |
| JP | 2016524960 A | 8/2016 |
| JP | 2016527990 A | 9/2016 |
| WO | 2012091747 A1 | 7/2012 |

* cited by examiner

LEADLESS DELIVERY CATHETER WITH CONDUCTIVE PATHWAY

CROSS REFERENCE TO RELATED APPLICATIONS

The present application claims the benefit of and priority to U.S. Provisional Patent Application Ser. No. 62/439,259, filed Dec. 27, 2016, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including catheters and implantable devices.

In a first example, a catheter system for carrying an implantable leadless pacing device may comprise a tubular member including a lumen extending from a proximal end to a distal end thereof, a tubular distal holding structure extending distally of the distal end of the tubular member and defining a cavity, a leadless pacing device located at least partially within the cavity and having a proximal electrode and a distal electrode, and an electrical port extending through the tubular distal holding structure at a location proximal of the proximal electrode of the leadless pacing device. The electrical port may provide a conductive pathway for an electrical signal traveling through the tubular distal holding structure to and/or from the leadless pacing device.

Alternatively or additionally to any of the examples above, in another example, the catheter system may comprise an electrically conductive insert carried by the tubular distal holding structure. The electrically conductive insert may form at least part of the electrical port and the conductive pathway.

Alternatively or additionally to any of the examples above, in another example, the catheter system may comprise the electrically conductive insert being a ring insert carried by the tubular distal holding structure.

Alternatively or additionally to any of the examples above, in another example, the catheter system may comprise the ring insert having an opening about a central axis with the opening having a constant diameter at all circumferential locations. Further, the ring insert may have a first outer diameter at a first circumferential location and a second outer diameter at a second circumferential location, where the first outer diameter may be different than the second outer diameter.

Alternatively or additionally to any of the examples above, in another example, the catheter system may comprise a plurality of electrically conductive segments carried by the tubular distal holding structure. The plurality of electrically conductive segments may be circumferentially spaced around a central axis of the tubular distal holding structure and may form at least part of the electrical port and the conductive pathway.

Alternatively or additionally to any of the examples above, in another example, the catheter system may comprise each of the plurality of electrically conductive segments being spaced a same radial distance from the central axis of the tubular distal holding structure and each of the plurality of electrically conductive segments being located at a same axial location along the longitudinal axis of the tubular distal holding structure.

Alternatively or additionally to any of the examples above, in another example, the catheter system may comprise the electrical port being formed from an electrically conductive material of the tubular distal holding structure.

Alternatively or additionally to any of the examples above, in another example, the catheter system may comprise the tubular distal holding structure comprising a hub secured to the tubular member and a body portion secured to the hub and extending distally from the hub. The body portion may at least partially define the cavity.

Alternatively or additionally to any of the examples above, in another example, the catheter system may comprise the electrical port being located in the hub.

Alternatively or additionally to any of the examples above, in another example, the catheter system may comprise the hub including an electrically conductive insert forming the electrical port. The electrically conductive insert may extend through the hub to provide the conductive pathway between an interior of the tubular distal holding structure and an exterior of the tubular distal holding structure.

Alternatively or additionally to any of the examples above, in another example, the catheter system may comprise the electrically conductive insert being a ring insert.

Alternatively or additionally to any of the examples above, in another example, the catheter system may comprise the electrically conductive insert comprising one or more electrically conductive segments.

Alternatively or additionally to any of the examples above, in another example, the catheter system may comprise the hub comprising one or more pockets and each of the one or more pockets being configured to expose at least one of the electrically conductive segments.

Alternatively or additionally to any of the examples above, in another example, the catheter system may comprise the electrical port being located in the body portion.

In another example, a catheter for carrying an implantable leadless pacing device may comprise a tubular member including a lumen extending from a proximal end to a distal end thereof, a tubular distal holding structure extending distally of the distal end of the tubular member and defining a cavity, and an electrical port extending through a proximal portion of the tubular distal holding structure. The electrical port may provide a conductive pathway between an interior of the distal holding structure and an exterior of the distal holding structure.

Alternatively or additionally to any of the examples above, in another example, the catheter may comprise an electrically conductive insert carried by the tubular distal holding structure. The electrically conductive insert may form at least part of the electrical port and the conductive pathway.

Alternatively or additionally to any of the examples above, in another example, the catheter may comprise the tubular distal holding structure comprising a hub attached to and extending distally from the tubular member and a body portion attached to and extending distally from the hub. The electrical port may comprise one or more electrically conductive inserts extending through the hub to form the conductive pathway.

In another example, a method of forming a catheter for carrying an implantable leadless pacing device may comprise attaching a body portion to a hub structure such that the body portion extends distally from the hub structure and to form a distal holding structure defining a cavity. The method may further include forming an electrical port in the hub structure. The formed electrical port may have a conductive pathway extending between interior the tubular distal holding structure and exterior the tubular distal holding structure to form an electrical port in the hub.

Alternatively or additionally to any of the examples above, in another example, the method may comprise forming the electrical port in the hub structure by molding an electrically conductive insert into the hub structure.

Alternatively or additionally to any of the examples above, in another example, the method may comprise forming the electrical port in the hub structure by forming one or more pockets in the hub structure and exposing an electrically conductive segment in each of the one or more pockets.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
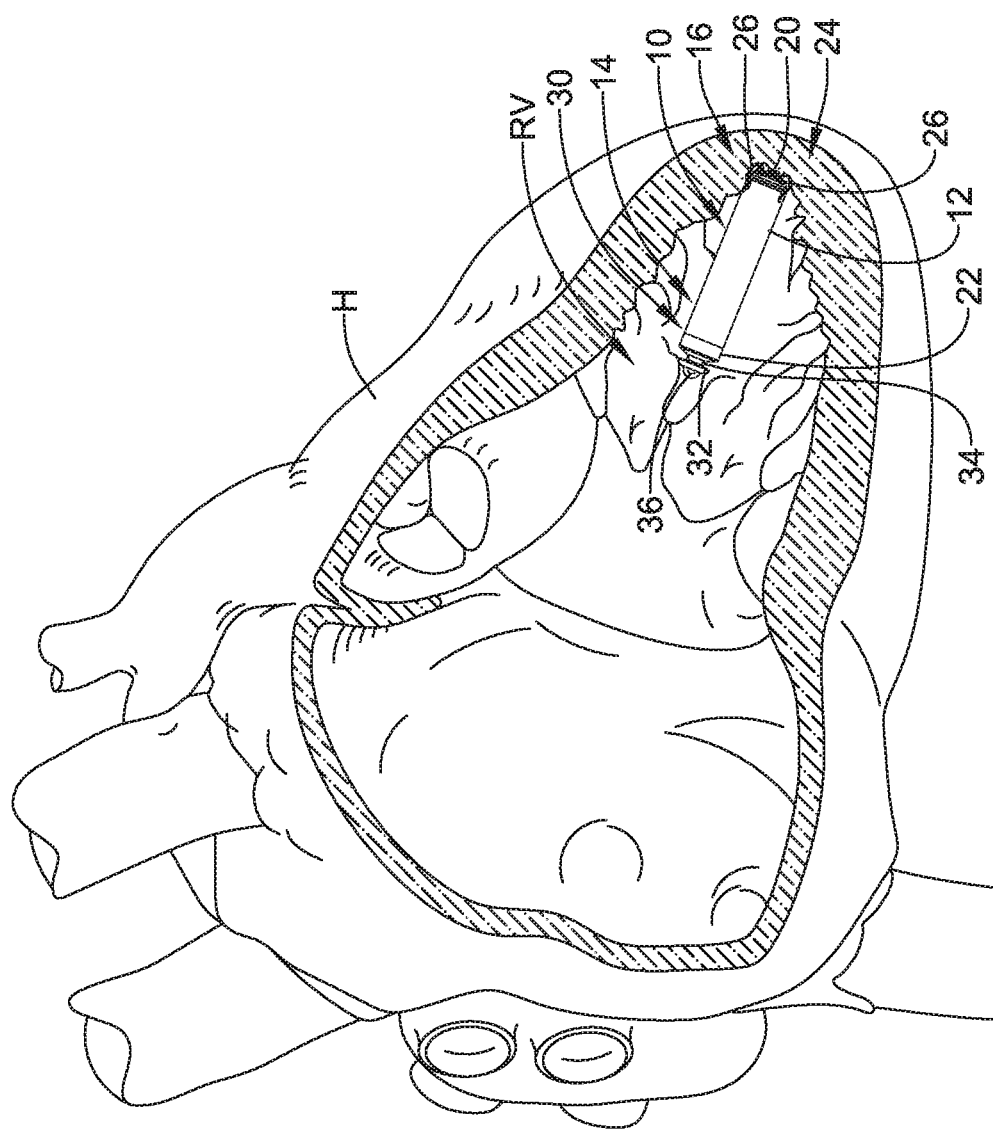
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
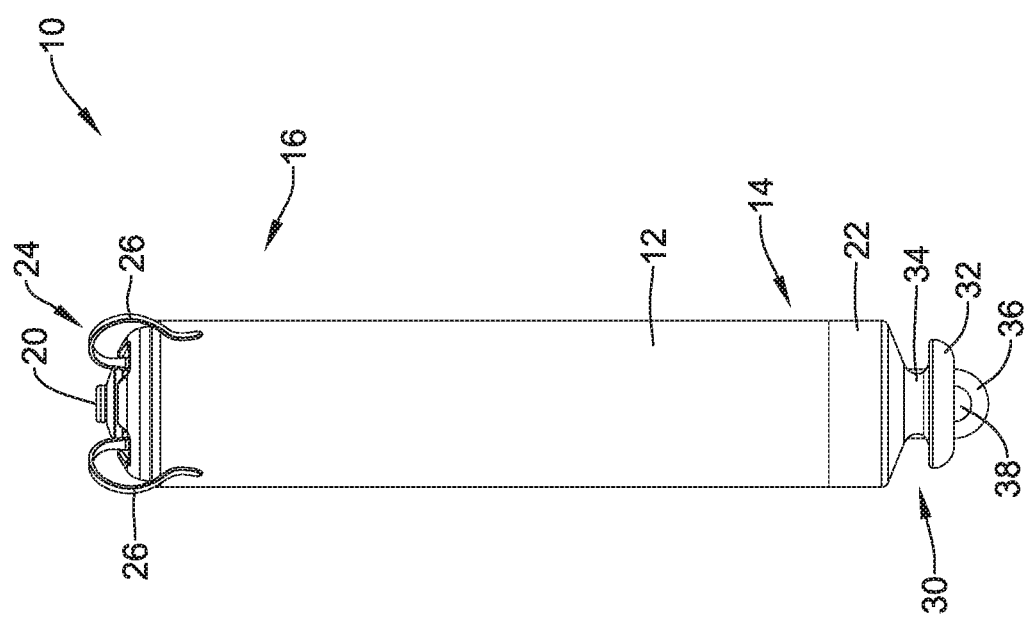
FIG. 2 is a side view of an example implantable leadless cardiac pacing device.

FIG. 1 illustrates an example implantable leadless cardiac pacing device 10 (e.g., a leadless pacemaker) implanted in a chamber of a heart H, such as the right ventricle RV. A side view of the illustrative implantable device 10 is shown in FIG. 2. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue. In some cases, electrical signals may travel between one or more of the electrodes 20, 22 and a remote device.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more hooks or tines 26 anchored into the cardiac tissue of the heart H to attach the implantable device 10 to a tissue wall. In other instances, the fixation mechanism 24 may include one or more passive tines configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. Although the docking member 30 may take on various forms, the docking member 30 may, for example, extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10.

The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12, but this is not required.

The docking member 30 may be configured to facilitate delivery of the implantable device 10 to the intracardiac site and/or retrieval of the implantable device 10 from the intracardiac site. Docking members 30, other than those described above, are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 3:
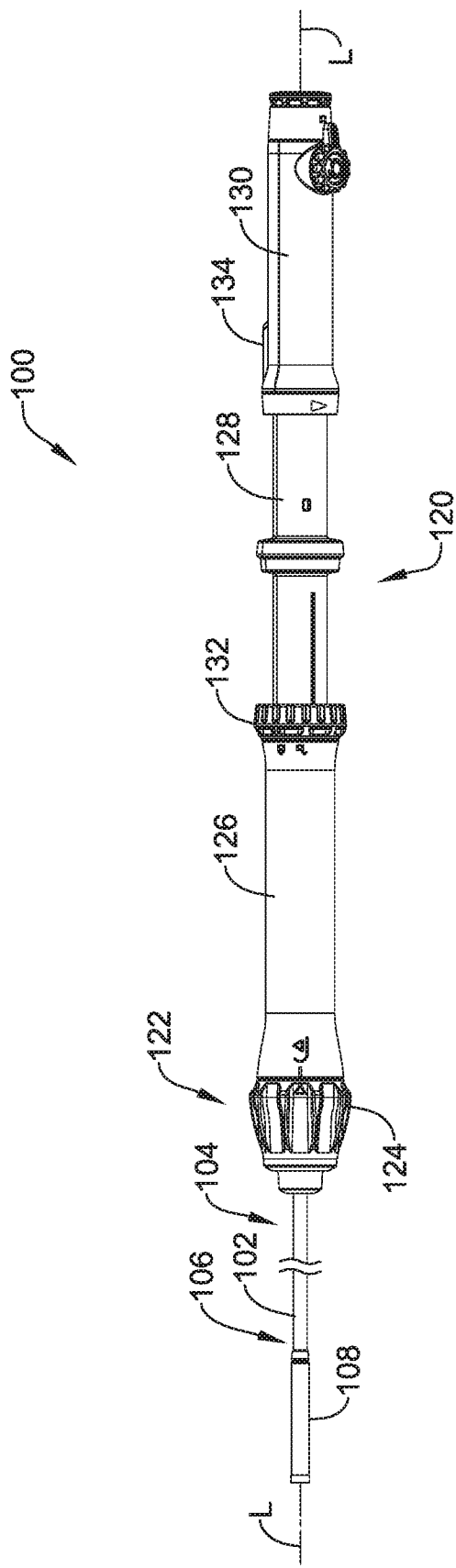
FIG. 3 is a plan view of an example delivery device for an implantable leadless cardiac pacing device.

FIG. 3 is a plan view of an illustrative delivery device 100, such as a catheter, that may be used to deliver the implantable device 10. The delivery device 100 may include an outer tubular member 102 having a proximal section 104 and a distal section 106. An intermediate tubular member 110 may be longitudinally slidably disposed within a lumen 150 of the outer tubular member 102 (see e.g., FIG. 4). An inner tubular member 116 may be longitudinally slidably disposed within a lumen 152 of the intermediate tubular member 110 (see e.g., FIG. 4). A distal holding section 108 may be attached to a distal end portion of the intermediate tubular member 110. In some cases, the distal holding section 108 may be tubular. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g., FIG. 4).

Figure 4:
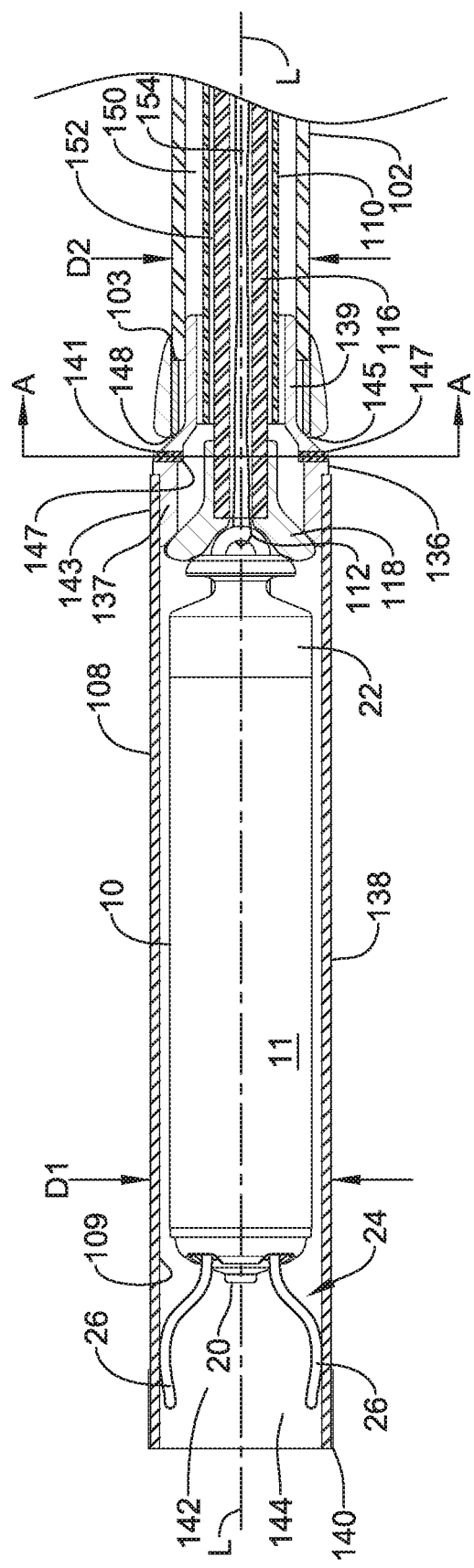
FIG. 4 is a partial cross-sectional side view of the distal portion of the delivery device of FIG. 3.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g., FIG. 4). The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The distal holding section 108 (e.g., a tubular distal holding structure) may extend along a longitudinal axis L (e.g., a central axis) and may be configured to receive the implantable device 10 therein. For example, referring to FIG. 4, which illustrates a partial cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 (e.g., a sleeve) and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 140 of the delivery device 100 may come into contact with tissue adjacent the target site (e.g. cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section 108. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is rounded or includes a curvature configured to be more atraumatic to tissue.

In some embodiments, all or a portion of the distal holding section 108 may include an inner surface 109 that may be configured to resist getting caught on the fixation mechanism 24, such as the one or more hooks or tines 26 on the device 10, and an exterior surface 11 (e.g., an outer surface) of the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor implantable device 10 within a target region (e.g., a region of the heart such as the right ventricle). The inner tubular member 116 may have a lumen 154 extending from a proximal end to a distal portion 118 thereof. A tether 112 or other retaining feature may be used to releasably secure the device 10 to the delivery device 100. In some instances, the tether 112 may be a single or unitary length of material that may extend from a proximal end of the lumen 154, out through the distal portion 118, through the opening 38 of the device 10 and return to the proximal end of the inner tubular member 116 through the lumen 154 such that both ends of the tether 112 are positioned adjacent to the third hub portion 130. In some instances, as will be discussed in more detail below, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 3, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis L of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 4, the distal holding section 108 may be affixed to a distal end portion of the intermediate tubular member 110. The distal holding section 108 may include a hub portion 136 and a tubular body portion 138. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some instances, the hub portion 136 may be formed from a metal or metal alloy while the body portion 138 may be formed from a polymeric material, although this is not required. Alternatively, or in addition, the hub portion 136 be formed from a polymeric material with a metal or metal alloy insert 141.

The hub portion 136 of the distal holding section 108 may include one or more electrical ports 147 extending through the distal holding section 108 (e.g., from interior or within the distal holding section 108 to exterior the distal holding section 108) and made from an electrically conductive material (e.g., an electrically conductive polymer, an electrically conductive metal, or an electrically conductive metal alloy). In one example, the insert 141 may form one or more of the electrical ports 147. The radial thickness of the insert 141 may be greater than or equal to the radial thickness of the hub portion 136 directly adjacent to the insert 141 such that a radially inward surface of the insert 141 and a radially outward surface of the insert 141 are exposed from and not covered by the material of the hub portion 136. In another example, a hub formed from an electrically conductive metal or electrically conductive metal alloy may form one or more of the electrical ports 147.

Figure 5:
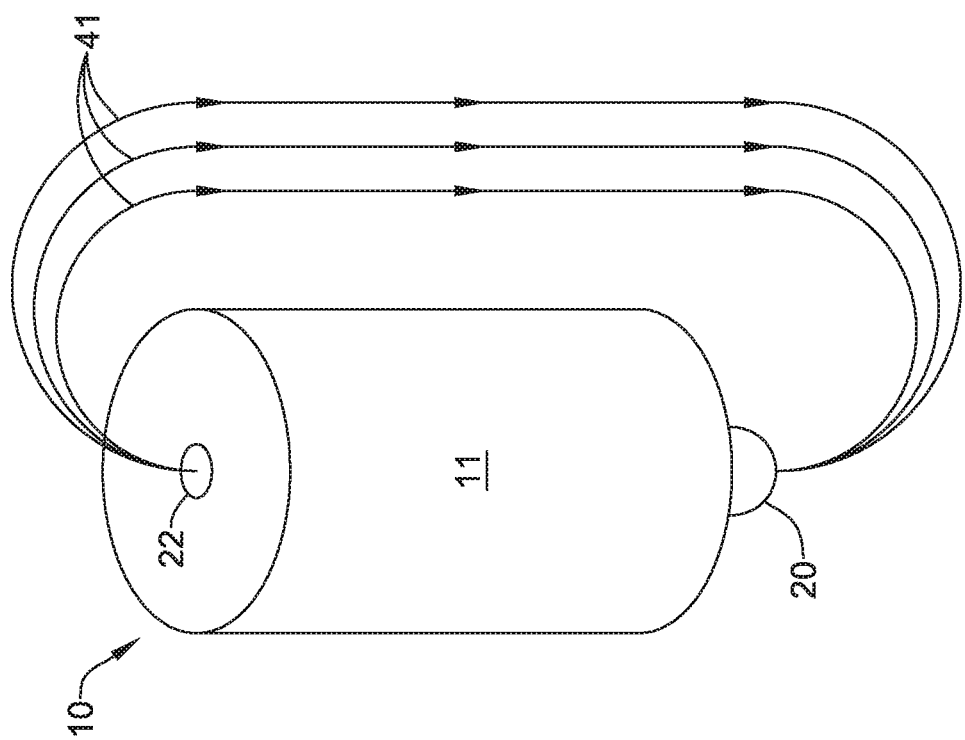
FIG. 5 is a perspective view of an example schematic implantable leadless cardiac pacemaker deploying electrical signals.

FIG. 5 depicts a schematic implantable device 10. The implantable device 10 may include a first electrode 20 at a distal end 16 and a second electrode 22 at a proximal end 14. Field lines 41, as shown in FIG. 5, depict electrical signals (e.g., current) traveling from the second electrode 22 to the first electrode 20. When the implantable device 10 is implanted in a patient, the current deployed from the implantable device 10, as by field lines 41, may be applied to a patient (e.g., a patient's heart) to provide therapy. Additionally or alternatively, field lines 41 may be utilized to sense one or more characteristics of the heart or tissue around the implantable device 10.

Further, in some cases and although not shown, electrical signals may travel between one or more of the first electrode 20 and second electrode 22 and a device (e.g., a programmer or other device) that is remote from the implantable device 10. Prior to deployment of the implantable device 10 from the distal holding section 108 or otherwise while the leadless pacemaker is within a sleeve, it may be desirable to communicate with the implantable device 10 via a device that is exterior a patient or otherwise remote from the implantable device 10. Such communication may allow for assessment of device status (e.g., determining if the implantable device 10 is functional, determining the ability of the implantable device 10 to turn on if required during delivery and/or implantation, etc.) prior to releasing the fixation mechanisms into a patient (e.g., into a patient's myocardium), which may facilitate reducing a time for an implant procedure implanting the implantable device.

Figure 6:
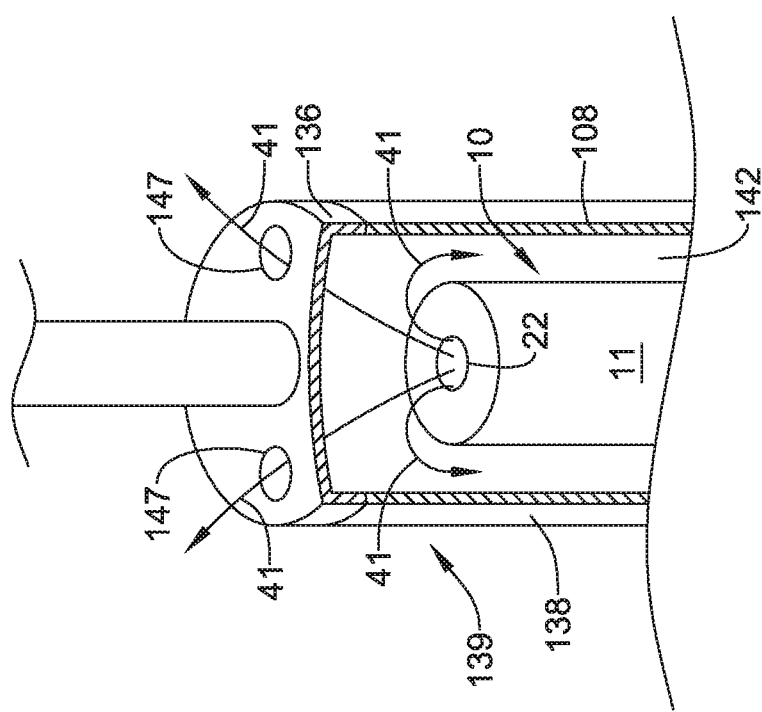
FIG. 6 is a perspective partial cross-sectional view of an example schematic implantable leadless cardiac pacemaker in a holding chamber of a delivery device, where the implantable leadless cardiac pacemaker is deploying electrical signals.

FIG. 6 depicts a schematic view of an implantable device 10 located within the distal holding section 108 of a delivery device 100, where the distal holding section 108 is pictured in cross-section. Field lines 41 in FIG. 6 may depict an electrical signal deployed from the implantable device 10 as passing through electrical ports 147 and thus, facilitating communication between the first electrode 20 and the second electrode 22 and/or between the implantable device 10 and a remote device.

As shown in FIG. 6, the electrical ports 147 may be located in the distal holding section 108 at a location adjacent to or proximal of the proximal end of the implantable device 10 when the implantable device 10 is positioned within the distal holding section 108 (e.g., within a cavity 142 of the distal holding section 108). In some cases, metal or metal alloy of the distal hub portion 136 and/or the insert 141 may form the electrical ports 147 and allow electrical signals (e.g., current) to pass from interior the distal holding section 108 to exterior the distal holding section 108. Additionally, or alternatively, the electrical ports 147 may be located along the body portion 138 of the distal holding section 108, at a location adjacent to and/or proximal of the second electrode 22 when the implantable device 10 is positioned within the distal holding section 108.

Although the distal holding section 108 may include one or more electrical ports 147 adjacent a proximal end portion 139 of the distal holding section 108 to facilitate communicating with the leadless pacemaker while it is within the distal holding section 108, signal losses and communication impairment may be observed. Such signal losses and/or communication impairment may be due, at least in part, to current crowding inside the distal holding section 108. As such, the distal holding section 108 may include one or more barriers (not shown) between the first electrode 20 (e.g., as depicted in FIG. 5) and the second electrode 22 to prevent or limit electricals signals from traveling within the distal holding section 108 between the first electrode 20 and the second electrode 22.

FIGS. 7-12 depict various illustrative configurations of the insert 141 and/or the hub portion 136. These illustrative configurations of the insert 141 and/or the hub portion 136, along with others, may be usable individually and/or together to form the insert 141 and/or the hub portion 136 of the distal holding section 108.

The insert 141 may take on any form that facilitates forming or forms an electrical port 147 providing a conductive pathway for electrical signals (e.g., current) traveling through the tubular distal holding section 108. The insert 141 may be part of, may be affixed to, and/or may extend from the distal holding section 108. Examples of inserts 141 may include, but are not limited to, electrically conductive rings, electrically conductive segments, and/or other electrically conductive material configured to facilitate electrical signal travel between an interior and an exterior of the distal holding section 108.

FIGS. 7-10 are cross-sectional views taken along line A-A in FIG. 4, which depict various illustrative configurations of the insert 141. In some cases, the insert 141 may be a ring shape, triangular shape, square shape, two or more different shapes, a single piece of material, separate pieces of material, and/or one or more other configurations. Other shapes and/or configurations are contemplated and may be utilized.

Figure 7:
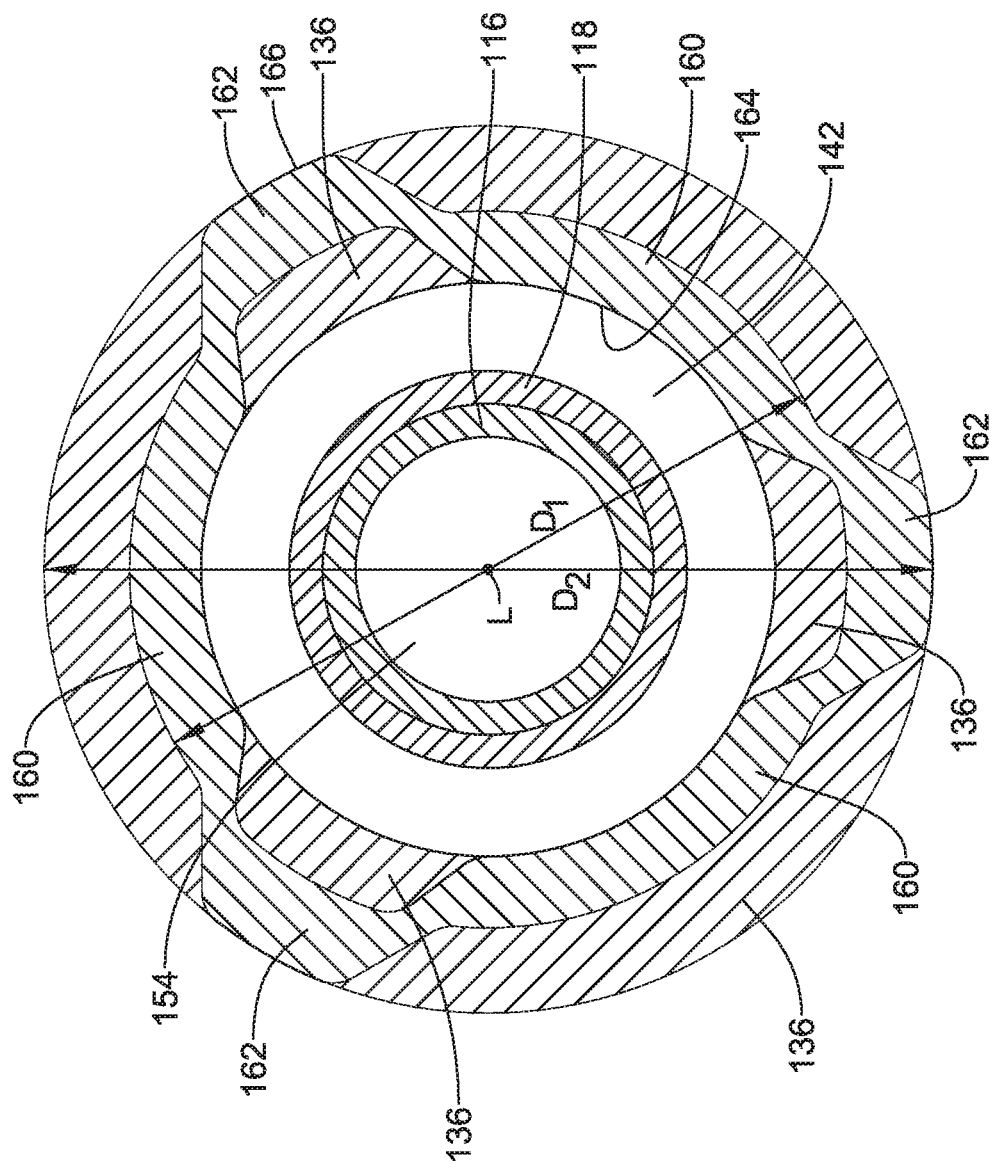
FIG. 7 is a cross-sectional view of the distal portion of the delivery device of FIG. 3, taken along line A-A in FIG. 4 showing an example configuration of an insert and a distal hub portion of the delivery device.
Figure 7A:
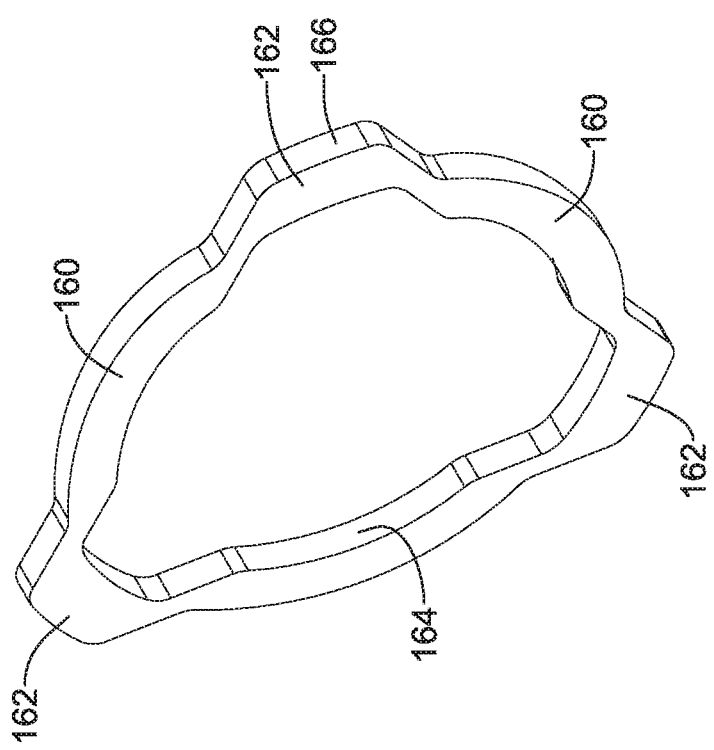
FIG. 7A is a perspective view of the insert of the embodiment of FIG. 7.
Figure 7B:
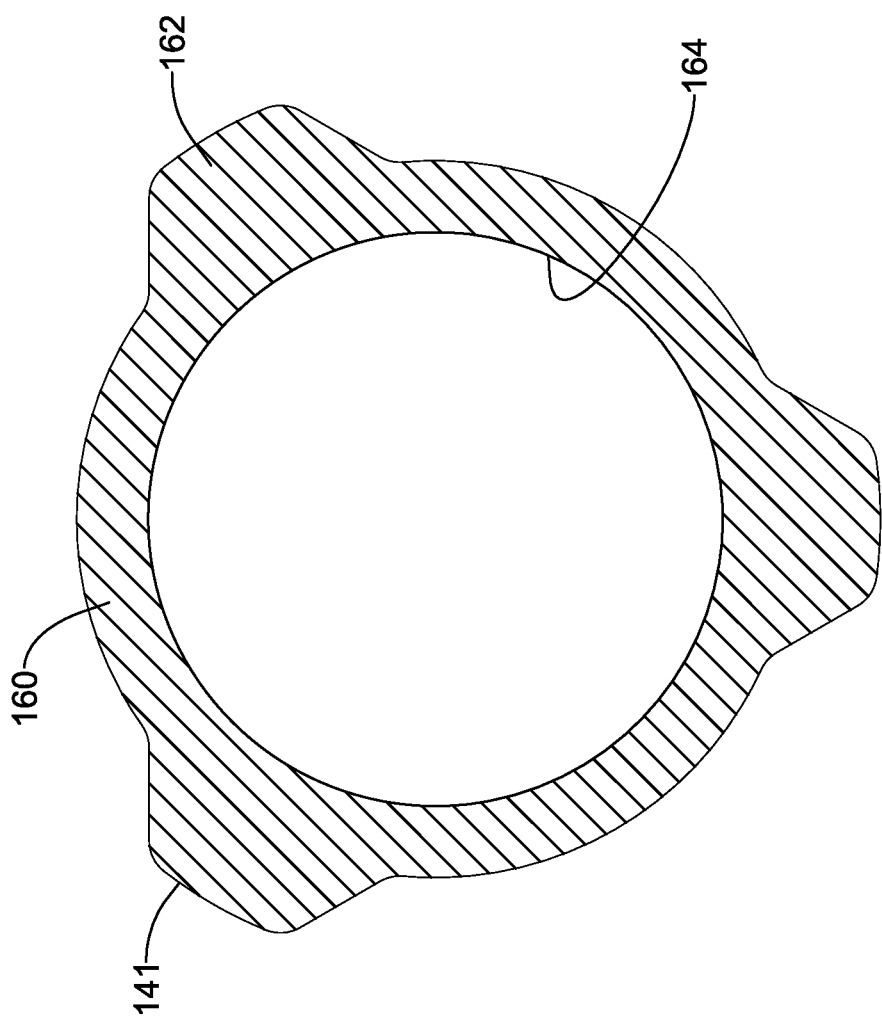
FIG. 7B is a cross-sectional view of an alternative insert.

The schematic cross-sectional view shown in FIG. 7 depicts one example of a metal or metal alloy insert 141 (e.g., at least partially formed of an electrically conducting material) located at least partially within (e.g., embedded in) a polymer material or other material of the distal holding section 108 (e.g., material of the hub portion 136 or other portion of the distal holding section 108). The insert 141 depicted in FIG. 7 has a ring shape with an inner ring 160 having an inner circumference 164 having a radius from the longitudinal axis L, where one or more, or a plurality of projections 162 (e.g., three projections 162) extend radially outward from the inner ring 160. FIG. 7A is a perspective view of the insert 141, showing the projections 162 extending radially outward. FIG. 7B is a cross-sectional view of an alternative insert 141 having an inner ring 160 and projections 162 as shown in FIG. 7A, but with the inner circumference 164 defining an opening having a constant diameter at all circumferential locations.

When the insert 141 is encased within material of the distal holding section 108 (e.g., within the hub portion 136 or other portion), one or more portions of the insert 141 may be exposed from the material of the distal holding section 108 interior of the distal holding section 108 and exterior of the distal holding section 108 to form the electrical port(s) 147. For example, the surface along the inner circumference 164 and a surface on the outer circumference 166 of the projections 162 may be exposed for electrical current to pass therethrough. In other words, the insert 141 may include an exposed conductive surface on the exterior of the distal holding section 108 and an exposed conductive surface on the interior of the distal holding section 108 (e.g., in the cavity). However, this is not required and fewer than all of the projections 162 may be exposed from the material of the distal holding section 108 interior the distal holding section 108 and/or exterior the distal holding section 108.

The insert 141 of FIG. 7 may have a first outer diameter D1 having a first length and a second outer diameter D2 having a second length that is different than the first length. In some cases, the different length diameters may be due to projections 162 extending from the inner ring 160. This is not always the case though and different length outer diameters may be due to one or more other configurations of the insert 141.

The polymeric material of the hub portion 136 may be disposed around the insert 141 to thereby embed the insert 141 into the hub portion 136. For example, as shown in FIG. 7, a first portion of the polymeric material of the hub portion 136 may be located radially inward of a portion of the insert 141 (such as radially inward of the projections 162, while a second portion of the polymeric material may be located radially outward of a portion of the insert 141 (such as circumferentially between the projections 162), with the first and second portions being a continuous portion of the hub portion 136 encasing the insert 141.

Figure 8:
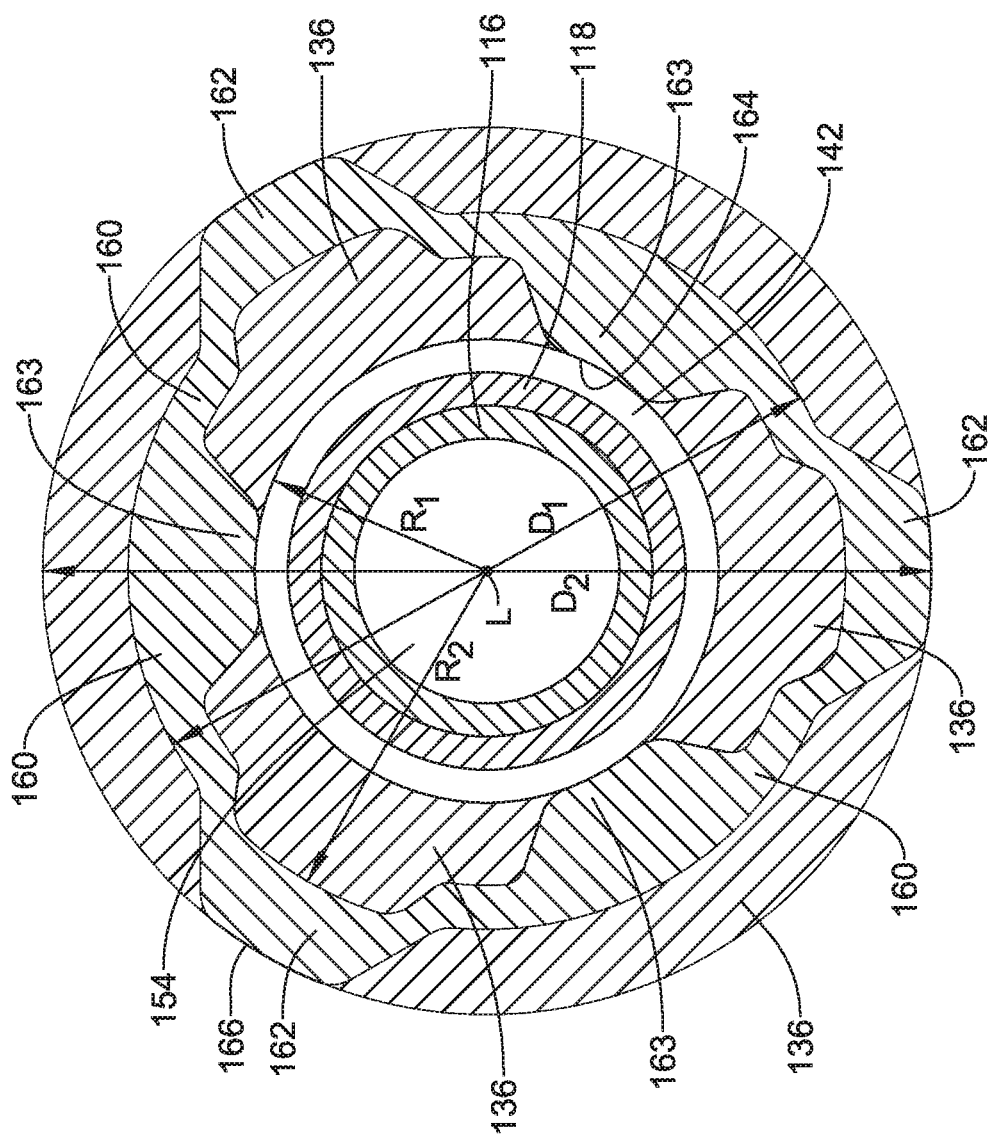
FIG. 8 is a cross-sectional view of the distal portion of the delivery device of FIG. 3, taken along line A-A in FIG. 4 showing an example configuration of an insert and a distal hub portion of the delivery device.

The schematic cross-sectional view shown in FIG. 8 depicts a further example of a metal or metal alloy insert 141 (e.g., at least partially formed of an electrically conducting material) located at least partially within (e.g., embedded in) a polymer material or other material of the distal holding section 108 (e.g., material of the hub portion 136 or other portion of the distal holding section 108). The insert 141 depicted in FIG. 8 has a ring shape about the longitudinal axis L with a plurality of projections 162 (e.g., three projections 162) extending radially outward from the inner ring 160 and a plurality of projections 163 (e.g., three projections 163) extending radially inward from the inner ring 160. When the insert 141 is encased within the distal holding section 108 (e.g., within the hub portion 136 or other portion), one or more portions of each of the projections 162 may be exposed from the material of the distal holding section 108 on the exterior of the distal holding section 108 and one or more portions of each of the projections 163 may be exposed from the material of the distal holding section 108 on the interior the distal holding section 108 and open into the cavity 142 to form the electrical port(s) 147. For example, a surface along the inner circumference 164 of the projections 163 and a surface on the outer circumference 166 of the projections 162 may be exposed for electrical current to pass therethrough. In other words, the insert 141 may include an exposed conductive surface on the exterior of the distal holding section 108 and an exposed conductive surface on the interior of the distal holding section 108 (e.g., in the cavity). However, this is not required and fewer than all three of the projections 162 may be exposed from the material of the distal holding section 108 exterior of the distal holding section 108 and fewer than all three of the projections 163 may be exposed from the material of the distal holding section 108 interior of the distal holding section 108.

The inner circumference 164 of the insert 141 in FIG. 8 may have a first inner radius R1 having a first length and a second inner radius R2 having a second length that is different than the first length. In some cases, the different length radii may be due to projections 163 extending radially inward from the inner ring 160. This is not always the case though and different length inner radii may be due to one or more other configurations of the insert 141.

As shown in FIG. 8, the insert 141 may have a first outer diameter D1 having a first length and a second outer diameter D2 having a second length that is different than the first length. In some cases, the different length diameters may be due to projections 162 extending radially outward from the inner ring 160. This is not always the case though and different length outer diameters may be due to one or more other configurations of the insert 141.

Figure 9:
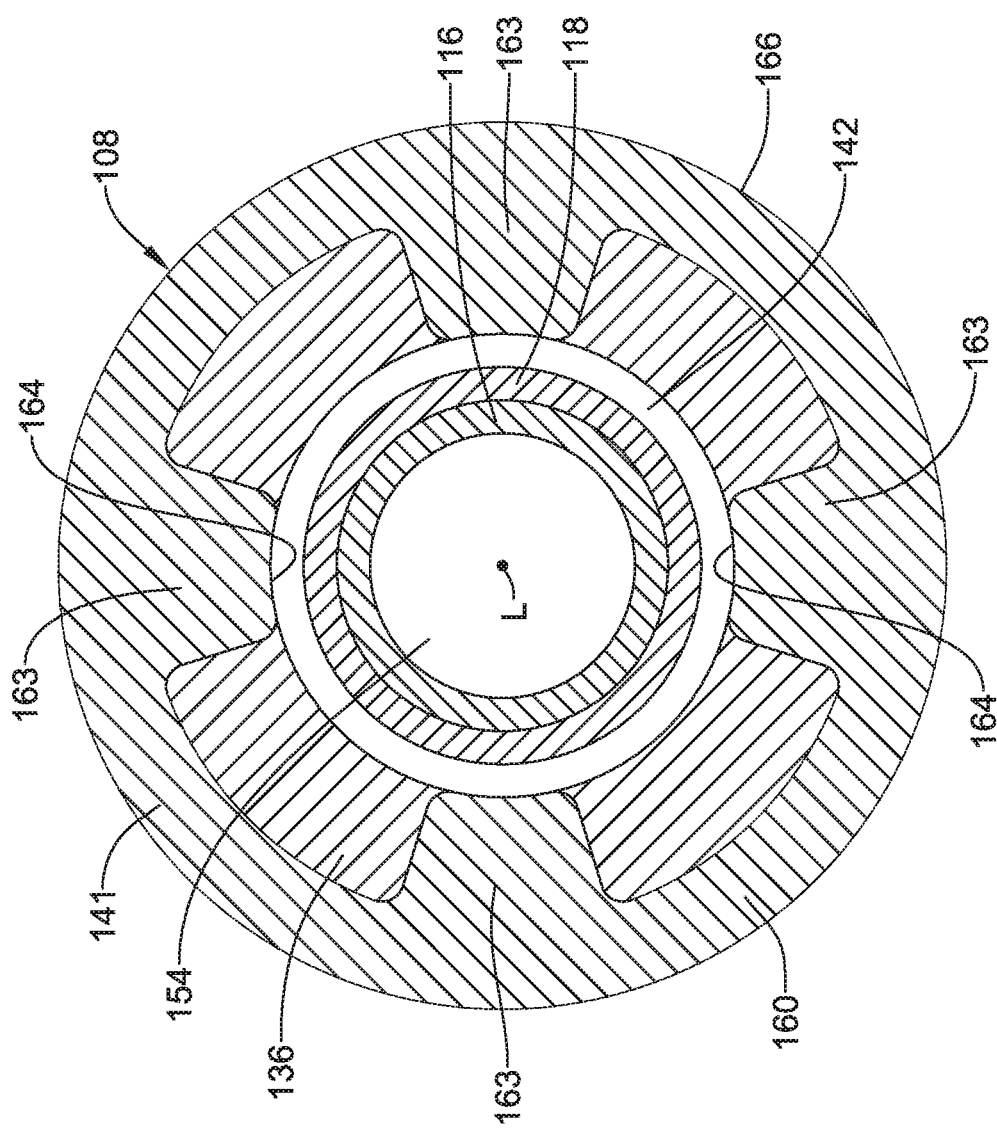
FIG. 9 is a cross-sectional view of the distal portion of the delivery device of FIG. 3, taken along line A-A in FIG. 4 showing an example configuration of an insert and a distal hub portion of the delivery device.

The schematic cross-sectional view shown in FIG. 9 depicts one example of a metal or metal alloy insert 141 (e.g., at least partially formed of an electrically conducting material) located at least partially within (e.g., embedded in) a polymer material or other material of the distal holding section 108 (e.g., material of the hub portion 136 or other portion of the distal holding section 108). The insert 141 depicted in FIG. 9 has a ring shape with an outer ring 160 having an outer circumference 166 having a constant radius from the longitudinal axis L (e.g., the insert 141 depicted may not have any projections extending radially outward from the outer ring 160. Additionally, the insert 141 of FIG. 9 may have an inner circumference 164 where one or more, or a plurality of projections 163 (e.g., four projections 163) extend radially inward from the inner ring 160.

When the insert 141 is encased within the distal holding section 108 (e.g., within the hub portion 136 or other portion), one or more portions of each of the projections 163 may be exposed from the material of the distal holding section 108 interior the distal holding section 108 and exterior the distal holding section 108 to form the electrical port(s) 147. In one example, at least a portion of the outer ring 160 may be exposed from the material of the distal holding section 108 exterior of the distal holding section 108 and at least a portion of the projections 163 may be exposed from the material of the distal holding section 108 interior of the distal holding section 108. In other words, the insert 141 may include an exposed conductive surface on the exterior of the distal holding section 108 and an exposed conductive surface on the interior of the distal holding section 108 (e.g., in the cavity). In some instances, two or more portions of the outer ring 160 may be exposed from the material of the distal holding section 108 interior and exterior thereof, where each of the two or more exposed portions of the outer ring 160 may be at circumferential locations that are circumferentially spaced and separated by unexposed portions of the inner ring 160. Polymeric material of the hub portion 136 may be located circumferentially between the projections 163 radially inward of the outer ring 160 to embed the insert 141 in the hub portion 136.

Figure 10:
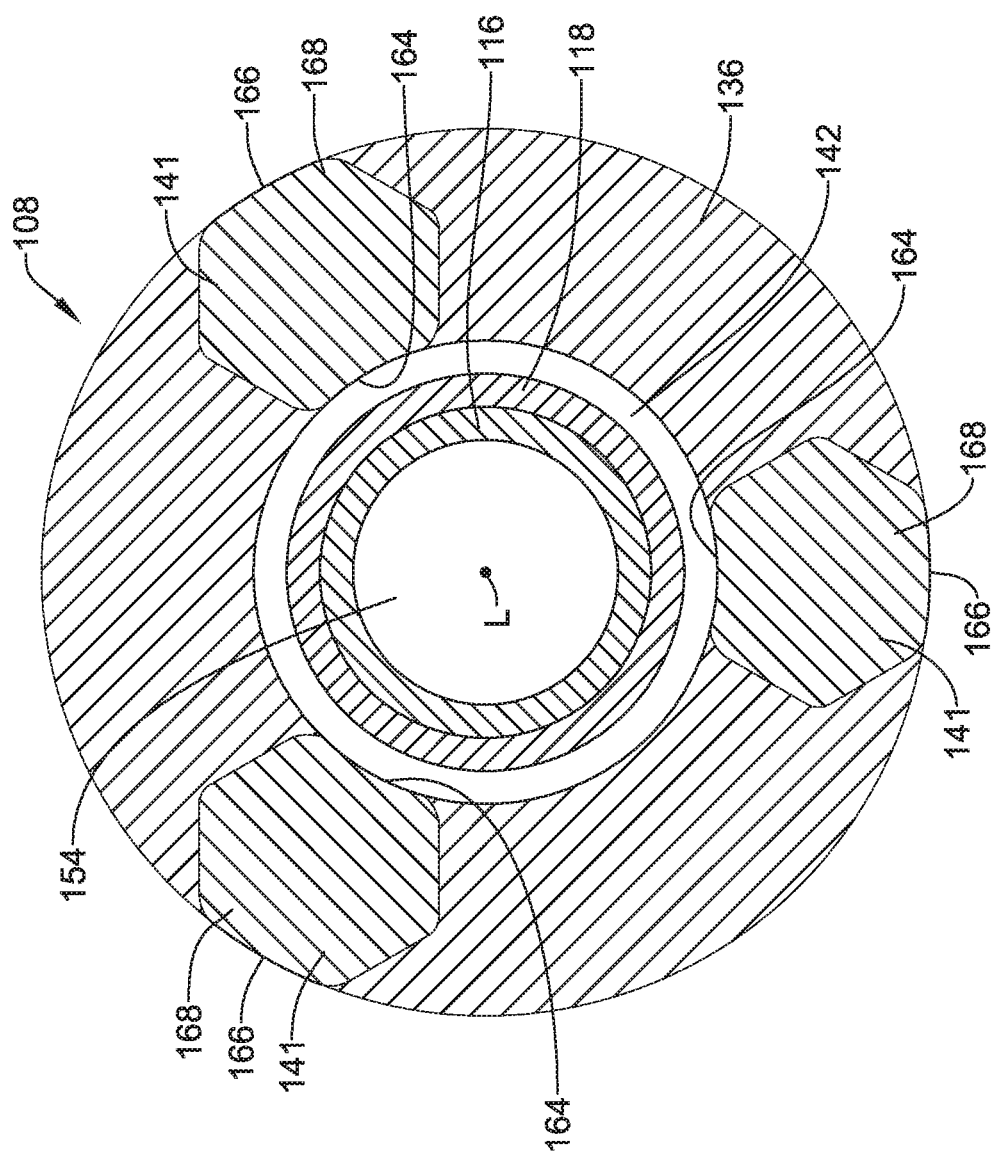
FIG. 10 is a cross-sectional view of the distal portion of the delivery device of FIG. 3, taken along line A-A in FIG. 4 showing an example configuration of an insert and a distal hub portion of the delivery device.

The schematic cross-sectional view shown in FIG. 10 depicts one example of a metal or metal alloy insert 141 (e.g., at least partially formed of an electrically conducting material) located at least partially within (e.g., embedded in) a polymer material or other material of the distal holding section 108 (e.g., material of the hub portion 136 or other portion of the distal holding section 108). The insert 141 depicted in FIG. 10 may include a plurality of discrete segments 168 (e.g., electrically conductive segments). Each of the discrete segments 168 may be spaced away from adjacent segments 168. Each of the segments 168 may have an arced inner circumference 164 having a radius from the longitudinal axis L and an arced outer circumference 166 having a radius from the longitudinal axis L. However, this is not required and one or more of the inner circumference 164 and the outer circumference 166 of one or more of the segments 168 may have a radius from the longitudinal axis L that differs from a similar one of the inner circumference 164 and the outer circumference 166. In one example, the inner circumference 164 and/or the outer circumference 166 of one or more of the segments 168 may be a straight line, which may result in the inner circumference 164 and/or the outer circumference 166 of a single segment 168 having different radii along a length thereof.

When segments 168 of the insert 141 are encased within material of the distal holding section 108 (e.g., within the hub portion 136 or other portion), one or more portions of each of the segments 168 may be exposed from the material of the distal holding section 108 interior of the distal holding section 108 and exterior of the distal holding section 108. In other words, each of the segments 168 of the insert 141 may include an exposed conductive surface on the exterior of the distal holding section 108 and an exposed conductive surface on the interior of the distal holding section 108 (e.g., in the cavity).

The electrical ports 147 may be formed within (e.g., on or in) the distal holding section 108 in any manner. In one example, the insert 141 may be inserted or otherwise located within the distal holding section 108 (e.g., the hub portion 136 or other portion) during the forming of the distal holding section 108 to form the electrical ports 147. In another example, the insert 141 may be added to the formed distal holding section 108 (e.g., the hub portion 136 or other portion) after the distal holding section 108 is formed or a portion thereof (e.g., the hub portion 136 or other portion) is formed to form the electrical ports 147.

Figure 11:
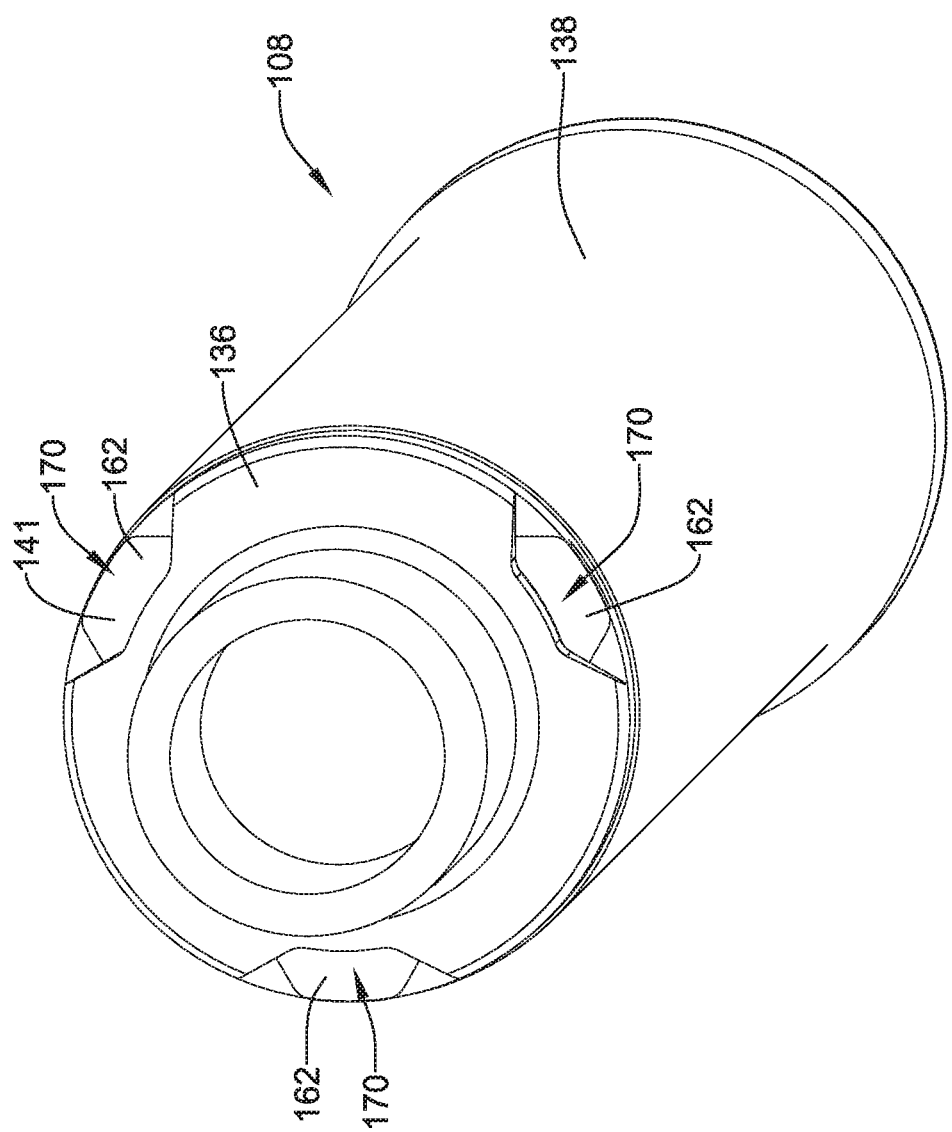
FIG. 11 is a plan view from a proximal end of an example schematic distal hub portion of a delivery device.

When the insert 141 is added to the formed distal holding section 108 or a portion thereof after the distal holding section 108 or the portion thereof is formed, the insert 141 may be positioned in one or more pockets formed in the distal holding section 108 or the portion thereof. FIG. 11 is a schematic view of an example distal holding section 108 including a body portion 138 and a hub portion 136 viewed from a proximal end of the hub portion 136. As may be seen from FIG. 11, the hub portion 136 may include a plurality of pockets 170 (e.g., three pockets 170 as shown in FIG. 11, but one or more pockets may be utilized) for receiving and/or exposing an insert 141 (not shown in FIG. 11) to form the electrical ports 147. The pockets 170 may be circumferentially spaced about the longitudinal axis L, but this is not required. When the pockets 170 are circumferentially spaced, as shown for example in FIG. 11, the pockets 170 may be configured to receive and/or expose ring segments 168. Although not shown, a single pocket may be formed in the hub portion 136 and an insert 141 having an inner ring 160 may be utilized and placed and/or exposed in the pocket. Further, the pockets 170 may have any shape and size configured to secure and/or expose inserts 141 within the distal holding section 108 to form one or more electrical ports providing a conductive pathway for electrical signals traveling between the cavity 142 of the distal holding section 108 to an exterior of the distal holding section at or near the hub portion 136. As shown in FIG. 11, the pockets 170 may be configured such that a proximally facing surface of the inert 141, such as the proximally facing surface of the projections 162 of the insert 141, may be exposed to an exterior of the distal holder section 108, as well as a radially facing surface of the projections 162 of the insert 141. Such a configuration may provide additional exposed surface area of the insert 141 for defining the conductive pathway.

Figure 12:
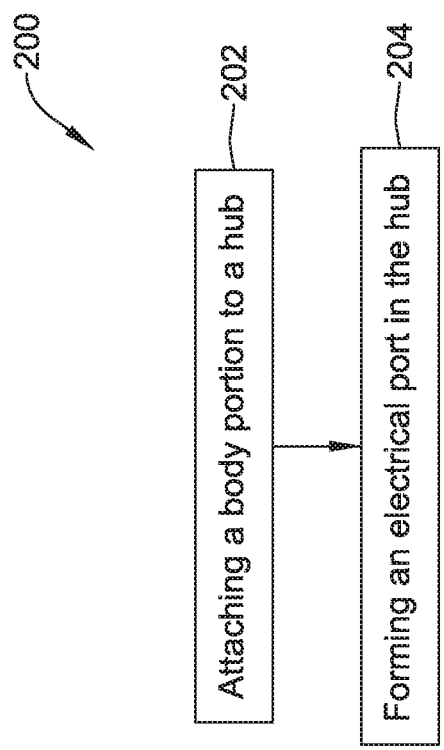
FIG. 12 is a schematic flow diagram of an illustrative method of forming a catheter for carrying an implantable device.

FIG. 12 depicts a method 200 of forming a catheter for carrying an implantable leadless pacing device 10. The method 200 may include attaching 202 the body portion 138 to the hub portion 136 to form the structure or a portion there of the distal holding section 108. The body portion 138 may be attached to the hub portion 136 in any manner including, but not limited to, with the use of welding techniques, molding techniques, melting techniques, adhesive techniques, and/or one or more other techniques.

Further, the method 200 may include forming 204 one or more electrical ports 147 in the hub portion 136. The formed one or more electrical ports may have a conductive pathway extending between an interior of the structure of the distal holding section 108 and exterior of the structure of the distal holding section 108.

Although the method 200 depicted in FIG. 12 includes forming the electrical ports 147 after attaching the body portion 138 to the hub portion 136, the electrical ports 147 may be formed prior to attaching the body portion 138 to the hub portion 136. In one example, the electrical ports 147 may be formed in or on one or more of the body portion 138 and the hub portion 136 and then, the body portion 138 may be attached to the hub portion 136.

As discussed above, the forming of the electrical ports 147 in the distal holding section 108 (e.g., the hub portion 136 or other portion) may be done in one or more manners. In one example, the insert 141 may be placed within a mold and the distal holding section or a portion thereof (e.g., the hub portion 136 or other portion) may be molded (e.g., injection molded or molded in one or more other manners) around the insert 141. In such instances, the mold may be configured to result in or facilitate exposing portions of the insert 141 interior and exterior of the material of the distal holding section 108.

Further in another example of forming electrical ports 147, the electrical ports 147 may be formed after the formation of the distal holding section 108 or a portion thereof (e.g., the hub portion 136 or other portion). As discussed above with respect to FIGS. 10 and 11, forming the electrical ports 147 in the hub portion 136 may include forming one or more pockets 170 in the hub structure 136. In some cases, the pockets 170 may be formed in the hub portion 136 during a molding procedure (e.g., injection molding or other molding procedure). Alternatively, the pockets 170 may be formed by an extraction process where material may be removed from the hub structure 136 after a portion of hub portion 136 has been formed. Once the one or pockets 170 have are formed in the hub portion 136, one or more inserts 141 (e.g., inserts 141 having an inner ring 160 and/or inserts 141 having ring segments 168) may be inserted into the one or more pockets 170 to form electrical ports 147 having a conductive pathway extending between interior the tubular distal holding section 108 and exterior the distal holding section 108.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex highdensity polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A catheter system for carrying an implantable leadless pacing device, the catheter system comprising:
    a tubular member including a lumen extending from a proximal end to a distal end thereof;
    a tubular distal holding structure extending distally of the distal end of the tubular member, the tubular distal holding structure defining a cavity;
    a leadless pacing device located at least partially within the cavity, the leadless pacing device having a proximal electrode and a distal electrode; and
    an electrical port extending through the tubular distal holding structure at a location proximal of the proximal electrode of the leadless pacing device;
    an electrically conductive insert carried by the tubular distal holding structure, wherein portions of the insert are covered by the tubular distal holding structure and one or more discrete portions of the insert are exposed to an exterior of the tubular distal holding structure to form at least part of the electrical port;
    wherein the electrical port provides a conductive pathway for an electrical signal traveling through the tubular distal holding structure to and/or from the leadless pacing device,
    wherein the exposed portions of the insert form at least part of the conductive pathway; and
    wherein the insert includes an annular ring having at least one radially extending projection, wherein the one or more discrete exposed portions include an exposed outer perimeter of the at least one radially extending projection.

2. The catheter system of claim 1, wherein the tubular distal holding structure comprises:
    a hub secured to the tubular member; and
    a body portion secured to the hub and extending distally from the hub; and
    wherein the body portion at least partially defines the cavity.

3. The catheter system of claim 2, wherein the electrical port is located in the hub.

4. The catheter system of claim 2, wherein:
    the electrically conductive insert extends through the hub to provide the conductive pathway between an interior of the tubular distal holding structure and an exterior of the tubular distal holding structure.

5. The catheter system of claim 1, wherein the leadless pacing device has a housing and the proximal electrode and the distal electrode of the leadless pacing device are both disposed on the housing, wherein the electrical port is located proximal of the proximal electrode of the leadless pacing device when the leadless pacing device is enclosed within the cavity of the tubular distal holding structure.

6. A catheter system for carrying an implantable leadless pacing device, the catheter system comprising:
    a tubular member including a lumen extending from a proximal end to a distal end thereof;
    a tubular distal holding structure extending distally of the distal end of the tubular member, the tubular distal holding structure defining a cavity;
    a leadless pacing device located at least partially within the cavity, the leadless pacing device having a proximal electrode and a distal electrode; and
    an electrical port extending through the tubular distal holding structure at a location proximal of the proximal electrode of the leadless pacing device;
    an electrically conductive insert carried by the tubular distal holding structure, wherein portions of the insert are covered by the tubular distal holding structure and one or more discrete portions of the insert are exposed to an exterior of the tubular distal holding structure to form at least part of the electrical port;

wherein the electrical port provides a conductive pathway for an electrical signal traveling through the tubular distal holding structure to and/or from the leadless pacing device, wherein the exposed portions of the insert form at least part of the conductive pathway; and wherein the one or more discrete exposed portions include an exposed proximally facing surface of the insert.

7. A catheter system for carrying an implantable leadless pacing device, the catheter system comprising:

a tubular member including a lumen extending from a proximal end to a distal end thereof;

a tubular distal holding structure extending distally of the distal end of the tubular member, the tubular distal holding structure defining a cavity;

a leadless pacing device located at least partially within the cavity, the leadless pacing device having a housing with a proximal electrode and a distal electrode disposed on the housing; and an electrical port extending through the tubular distal holding structure at a location proximal of the proximal electrode of the leadless pacing device when the leadless pacing device is fully enclosed within the cavity of the tubular distal holding structure;

an electrically conductive insert carried by the tubular distal holding structure, wherein portions of the insert are covered by the tubular distal holding structure and a plurality of discrete portions of the insert are exposed to an exterior of the tubular distal holding structure to form at least part of the electrical port;

wherein the electrical port provides a conductive pathway for an electrical signal traveling through the tubular distal holding structure to and/or from the proximal electrode of the leadless pacing device;

wherein the insert includes an annular ring having a plurality of radially extending projections, wherein each of the plurality of discrete exposed portions include (1) an exposed outer perimeter of one of the plurality of radially extending projections and/or (2) an exposed proximally facing surface of one of the plurality of radially extending projections.

8. A catheter system for carrying an implantable leadless pacing device, the catheter system comprising:

a tubular member including a lumen extending from a proximal end to a distal end thereof;

a tubular distal holding structure extending distally of the distal end of the tubular member, the tubular distal holding structure defining a cavity;

a leadless pacing device located at least partially within the cavity, the leadless pacing device having a proximal electrode and a distal electrode; and an electrical port extending through the tubular distal holding structure at a location proximal of the proximal electrode of the leadless pacing device;

an electrically conductive insert carried by the tubular distal holding structure, wherein portions of the insert are covered by the tubular distal holding structure and one or more discrete portions of the insert are exposed to an exterior of the tubular distal holding structure to form at least part of the electrical port, wherein the electrically conductive insert is a ring insert carried by the tubular distal holding structure;

wherein the electrical port provides a conductive pathway for an electrical signal traveling through the tubular distal holding structure to and/or from the leadless pacing device, wherein the exposed portions of the insert form at least part of the conductive pathway; and wherein:
the ring insert has an opening about a central axis;
the opening has a constant diameter at all circumferential locations; and
the ring insert has a first outer diameter at a first circumferential location and a second outer diameter at a second circumferential location, the first outer diameter is different than the second outer diameter.

9. A catheter system for carrying an implantable leadless pacing device, the catheter system comprising:

a tubular member including a lumen extending from a proximal end to a distal end thereof;

a tubular distal holding structure extending distally of the distal end of the tubular member, the tubular distal holding structure defining a cavity;

a leadless pacing device located at least partially within the cavity, the leadless pacing device having a proximal electrode and a distal electrode; and an electrical port extending through the tubular distal holding structure at a location proximal of the proximal electrode of the leadless pacing device;

an electrically conductive insert carried by the tubular distal holding structure, wherein portions of the insert are covered by the tubular distal holding structure and one or more discrete portions of the insert are exposed to an exterior of the tubular distal holding structure to form at least part of the electrical port;

wherein the electrical port provides a conductive pathway for an electrical signal traveling through the tubular distal holding structure to and/or from the leadless pacing device, wherein the exposed portions of the insert form at least part of the conductive pathway;

wherein the tubular distal holding structure comprises a hub secured to the tubular member and a body portion secured to the hub and extending distally from the hub, the body portion at least partially defining the cavity;

wherein the electrically conductive insert extends through the hub to provide the conductive pathway between an interior of the tubular distal holding structure and an exterior of the tubular distal holding structure;

wherein the electrically conductive insert is a ring insert; and wherein the hub comprises one or more pockets and each of the one or more pockets is configured to expose a portion of the ring insert.

\* \* \* \* \*